(12) United States Patent
Tseytlin

(10) Patent No.: US 9,143,542 B1
(45) Date of Patent: Sep. 22, 2015

(54) MEDIA CONTENT COLLABORATION

(71) Applicant: Google Inc., Mountain View, CA (US)

(72) Inventor: Yan Tseytlin, Wayne, NJ (US)

(73) Assignee: Google Inc., Mountain View, CA (US)

( * ) Notice: Subject to any disclaimer, the term of this patent is extended or adjusted under 35 U.S.C. 154(b) by 203 days.

(21) Appl. No.: 13/910,776

(22) Filed: Jun. 5, 2013

(51) Int. Cl.
 *H04L 29/06* (2006.01)
 *A61B 6/00* (2006.01)
 *G06Q 10/10* (2012.01)

(52) U.S. Cl.
 CPC .............. *H04L 65/403* (2013.01); *A61B 6/00* (2013.01); *G06Q 10/10* (2013.01)

(58) Field of Classification Search
 CPC .................................................... H04L 65/403
 See application file for complete search history.

(56) References Cited

U.S. PATENT DOCUMENTS

| | | | | |
|---|---|---|---|---|
| 8,798,401 | B1 * | 8/2014 | Johnson et al. | 382/305 |
| 2010/0030578 | A1 * | 2/2010 | Siddique et al. | 705/3 |
| 2011/0035264 | A1 * | 2/2011 | Zaloom | 705/14.12 |
| 2012/0321192 | A1 * | 12/2012 | Marshall et al. | 382/190 |
| 2013/0215116 | A1 * | 8/2013 | Siddique et al. | 345/420 |
| 2013/0239049 | A1 * | 9/2013 | Perrodin et al. | 715/800 |
| 2013/0283142 | A1 * | 10/2013 | Farzin et al. | 715/224 |
| 2013/0328932 | A1 * | 12/2013 | Kim et al. | 345/636 |
| 2013/0332857 | A1 * | 12/2013 | Kim et al. | 715/753 |
| 2013/0346508 | A1 * | 12/2013 | Li et al. | 709/205 |
| 2014/0040775 | A1 * | 2/2014 | Stoop et al. | 715/753 |
| 2014/0050419 | A1 * | 2/2014 | Lerios et al. | 382/276 |
| 2014/0129942 | A1 * | 5/2014 | Rathod | 715/720 |
| 2014/0133782 | A1 * | 5/2014 | Asver et al. | 382/309 |
| 2014/0245173 | A1 * | 8/2014 | Knodt et al. | 715/748 |
| 2014/0304618 | A1 * | 10/2014 | Carriero et al. | 715/753 |

OTHER PUBLICATIONS

WeVideo—Online Video Creation, www.wevideo.com, Last accessed Jun. 6, 2013, 2 pages.

* cited by examiner

*Primary Examiner* — David Phantana Angkool
(74) *Attorney, Agent, or Firm* — Amin, Turocy & Watson, LLP

(57) ABSTRACT

A system for media content collaboration is provided. The system includes a media component, a collaboration component, a permissions component and a finalization component. The media component receives uploaded media content from a first user. The collaboration component generates an online collaboration space for the uploaded media content. The permissions component generates and grants permissions to a second user to edit or augment the uploaded media content in the online collaboration space. The finalization component generates a final version of the uploaded media content based in part on modifications made by the second user.

20 Claims, 14 Drawing Sheets

MEDIA CONTENT COLLABORATION

TECHNICAL FIELD

This disclosure relates to system(s) and method(s) that facilitate collaboration for generating, modifying and/or distributing media content.

BACKGROUND

The internet and media enabled portable computing devices have dramatically altered the processes for generating and consuming media content. Additionally, the convenience of being able to upload, view and/or share media content via the internet, essentially on demand, has resulted in explosive growth of internet media consumption. Presently, users can generate media content using numerous types of devices, e.g., computers, cellular phones, cameras, portable computing devices, etc. Furthermore, users can upload media content from virtually anywhere at any time, as long as they have access to media capable device(s) with an internet connection. For example, millions (if not billions) of people around the world have capability to produce media content, and popular online media services (e.g., service providers) can receive many hours of newly uploaded user-generated content every minute. However, conventional online media services (e.g., conventional service providers) are merely repositories for the uploaded user-generated content. As such, in general, conventional online media services (e.g., conventional service providers) simply allow users to upload, view and/or share media content.

SUMMARY

The following presents a simplified summary of the specification in order to provide a basic understanding of some aspects of the specification. This summary is not an extensive overview of the specification. It is intended to neither identify key or critical elements of the specification, nor delineate any scope of the particular implementations of the specification or any scope of the claims. Its sole purpose is to present some concepts of the specification in a simplified form as a prelude to the more detailed description that is presented later.

In accordance with an implementation, a system includes a media component, a collaboration component, a permissions component and a finalization component. The media component receives uploaded media content from a first user. The collaboration component generates an online collaboration space for the uploaded media content. The permissions component generates and grants permissions to a second user to edit or augment the uploaded media content in the online collaboration space. The finalization component generates a final version of the uploaded media content based in part on modifications made by the second user. In an aspect, the system includes an identification component. The identification component identifies the second user, in connection with collaborating via the online collaboration space, based on an editing function associated with the second user.

In accordance with another implementation, a method provides for receiving uploaded media content from a first user, generating an online collaboration space for the uploaded media content, generating and granting permissions to a second user to edit or augment the uploaded media content in the online collaboration space, and generating a final version of the uploaded media content based in part on modifications made by the second user. In an aspect, the method provides for identifying the second user, in connection with collaborating via the online collaboration space, based on an editing function associated with the second user.

In accordance with yet another implementation, a system includes a media component, a collaboration component, a permissions component and a finalization component. The media component receives a video uploaded by a first user. The collaboration component generates a collaboration space for the video. The permissions component generates and grants permissions to a second user to alter or enhance the video in the collaboration space. The finalization component generates a final version of the video based in part on modifications made by the second user. In an aspect, the system includes an identification component that introduces the second user to the first user. The second user is identified based on an editing function associated with the second user.

The following description and the annexed drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

Numerous aspects, implementations, objects and advantages of the present invention will be apparent upon consideration of the following detailed description, taken in conjunction with the accompanying drawings, in which like reference characters refer to like parts throughout, and in which.

DETAILED DESCRIPTION

Figure 1:
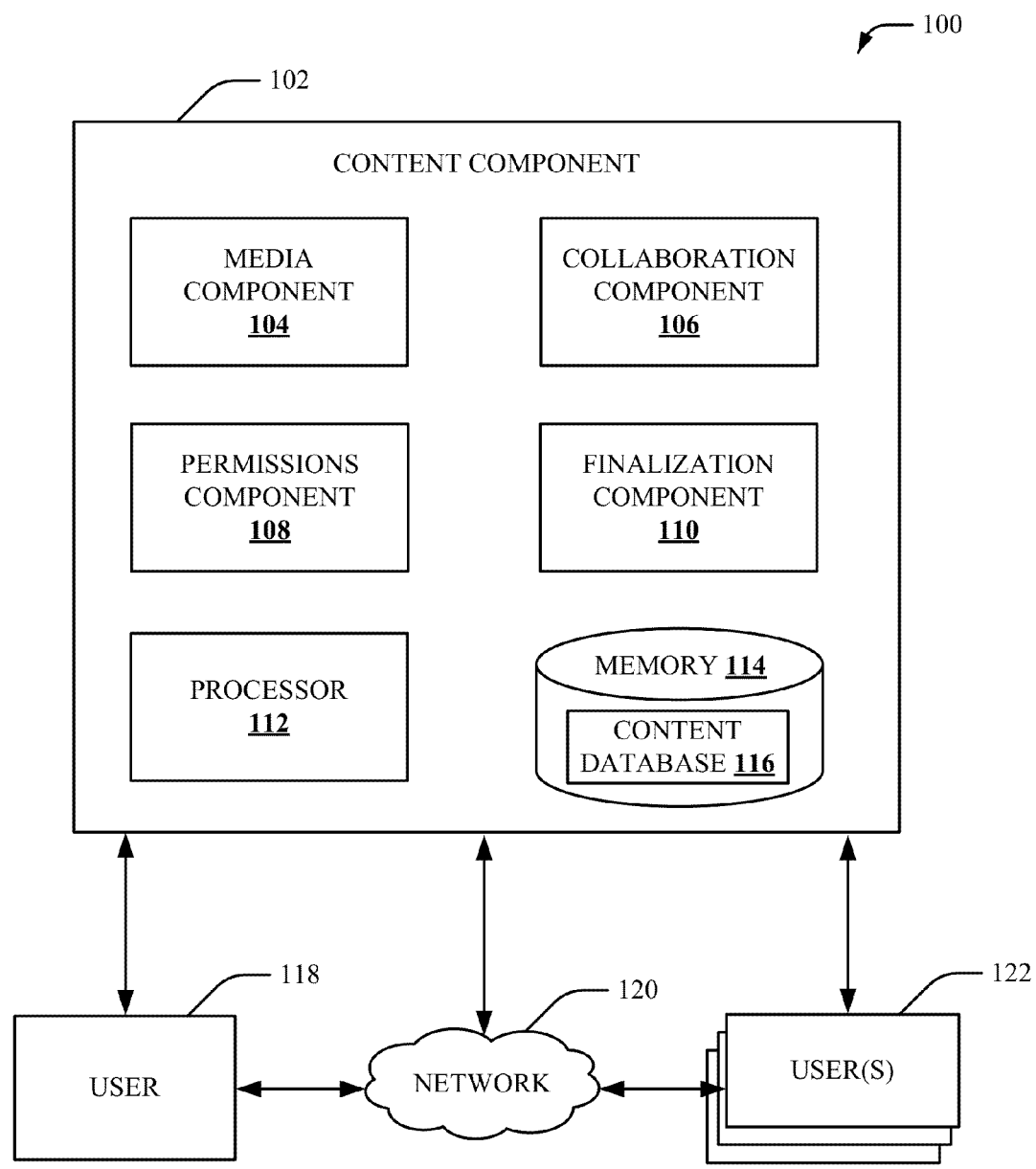
FIG. 1 illustrates a high-level block diagram of an example system to facilitate collaboration for generating and/or modifying media content, in accordance with various aspects and implementations described herein.

Various aspects of this disclosure are now described with reference to the drawings, wherein like reference numerals are used to refer to like elements throughout. In the following description, for purposes of explanation, numerous specific details are set forth in order to provide a thorough understanding of one or more aspects. It should be understood, however, that certain aspects of this disclosure may be practiced without these specific details, or with other methods, components, materials, etc. In other instances, well-known structures and devices are shown in block diagram form to facilitate describing one or more aspects.

Many conventional service providers allow users to upload media content (e.g., audio content and/or video content) to a server (e.g., a media content server). The media content can then be delivered (e.g., streamed) to other users. Service providers can provide network infrastructure for users to upload media content to the server (e.g., the media content server) and/or for users to view media content uploaded to the server (e.g., the media content server). However, conventional service providers are merely repositories for the uploaded media content (e.g., media content generated by a user device). As such, many conventional service providers simply allow users to upload, view and/or share the uploaded media content.

To that end, techniques that facilitate media content collaboration are disclosed. For example, a collaboration space (e.g., an internet collaboration space) can be generated to allow media content uploaded by a user to be edited and/or augmented by one or more others users (and/or the user that uploaded the media content). In an aspect, the collaboration space can include a cloud-based, real-time media editor. As such, the uploaded media content can be edited and/or augmented by one or more other users that did not upload the media content. Accordingly, a final version of the media content can be generated based on the edit(s) and/or augmentation(s) provided by the one or more other users and/or the user that uploaded the media content. As a result, the collaboration space can facilitate generation of improved media content via the collaboration space. In an aspect, the collaboration space can allow media content to be distributed (e.g., shared) by one or more other users that did not upload the media content. Therefore, the collaboration space can provide an online platform to connect users to collaboratively generate, modify and/or distribute media content.

Referring initially to FIG. 1, there is illustrated an example system 100 that can facilitate collaboration for generating and/or modifying media content, according to an aspect of the subject disclosure. In an aspect, the system 100 can be implemented on or in connection with one or more servers that host user-uploaded media content. For example, the system 100 can be employed by various systems, such as, but not limited to media content systems, media server systems, cloud-based systems, content management systems, network systems, computer network systems, communication systems, router systems, server systems, high availability server systems (e.g., Telecom server systems), Web server systems, file server systems, disk array systems, powered insertion board systems, and the like.

Specifically, the system 100 can provide a content component with a media feature (e.g., media component 104), a collaboration feature (e.g., collaboration component 106), a permissions feature (e.g., permissions component 108) and a finalization feature (e.g., finalization component 110) that can be utilized in, for example, a media content application (e.g., an online media content application). The media feature receives uploaded media content from a first user. The collaboration feature generates an online collaboration space for the uploaded media content. The permissions feature generates and grants permissions to a second user to edit or augment the uploaded media content in the online collaboration space. The finalization feature generates a final version of the uploaded media content based in part on modifications made by the second user.

In particular, the system 100 can include a content component 102 that includes at least a media component 104, a collaboration component 106, a permissions component 108 and a finalization component 110. Aspects of the systems, apparatuses or processes explained in this disclosure can constitute machine-executable component(s) embodied within machine(s), e.g., embodied in one or more computer readable mediums (or media) associated with one or more machines. Such component, when executed by the one or more machines, e.g., computer(s), computing device(s), virtual machine(s), etc. can cause the machine(s) to perform the operations described. System 100 can include memory 114 for storing computer executable components and instructions. System 100 can further include a processor 112 to facilitate operation of the instructions (e.g., computer executable components and instructions) by system 100.

The media component 104 can receive media content (e.g., user-generated media content). For example, the media component 104 can receive uploaded media content from a user 118 (e.g., a first user). In one example, the user 118 can be a user of a media sharing platform. The media content (e.g., media file) can include but is not limited to a video (e.g., a video file, a video clip, a video sample, etc.), audio (e.g., an audio file, an audio clip, an audio sample, etc.), an electronic book (e-book), a video game and/or other user-generated content. It is to be appreciated that the media file can be in any recognizable and suitable media file format (e.g., video file format or audio file format), codec compression format, etc. In an aspect, the media content can be stored in the content database 116. In one example, the uploaded media content can be associated with a media channel and/or a media playlist.

In an aspect, the media component 104 can receive the uploaded media content from the user 118 (e.g., the first user) via a network 120. The user 118 can utilize a device to capture (e.g., record) and/or upload the media content. For example, the device of the user 118 can include, but is not limited to, a cellular phone (e.g., a smartphone), a tablet, a personal computer (PC), a desktop computer, a laptop computer, a personal digital assistant (PDA), an electronic reader (e-reader), a camera, a media capable device, a portable computing device, an interactive television, an internet-connected television, a set-top box, a streaming media device, a gaming device, etc. For example, the user 118 can record (e.g., capture) a video using a smartphone and upload the video to the content component 102 (e.g., the media component 104) via the smartphone or another device.

The collaboration component 106 can generate a collaboration space (e.g., an online collaboration space, a cloud-based collaboration space, etc.) for the uploaded media content. For example, the collaboration component 106 can generate an online collaboration space that can be utilized via the network 120. The collaboration space can facilitate collaboration for viewing, modifying, augmenting, editing, distributing and/or sharing the uploaded media content. For example, the collaboration space can allow the user 118 and/or one or more other users (e.g., at least one user 122) to collaboratively manipulate and/or enhance the uploaded media content. For example, the at least one user 122 can use a device, such as but not limited to, a cellular phone (e.g., a smartphone), a tablet, a personal computer (PC), a desktop computer, a laptop computer, a camera, a media capable device, a portable computing device, an interactive television, an internet-connected television, a streaming media device, a gaming device, etc. to view, modify, augment, edit, distribute and/or share the uploaded media content. As such, the collaboration space can be a platform to connect (e.g., introduce) a plurality of users to collaboratively generate, edit and/or distribute media content. In an aspect, the collaboration space generated by the collaboration component 106 can include a real-time media editor (e.g., a real-time video editor).

The collaboration space can facilitate edit(s) and/or augmentation(s) to the uploaded media content. For example, the user 118 and/or the at least one user 122 can edit and/or augment the uploaded media content via the collaboration space. An edit or augmentation of the uploaded media content can include, but is not limited to, combining video and/or audio, trimming video and/or audio clips, rotating video clips, adding or removing visual effects, adding or removing text, adding or removing audio (e.g., music), inserting one or more transitions, stabilizing one or more video frames, etc. In one example, an edit or augmentation of the uploaded media content can include a video edit and/or an audio edit to the uploaded media content. In another example, an edit or augmentation of the uploaded media content can include a visual enhancement to the uploaded media content. In yet another example, an edit or augmentation of the uploaded media content can include reorganization of media frames of the uploaded media content. However, it is to be appreciated that an edit and/or augmentation of the uploaded media content can include other types of modifications. In an aspect, the user 118 can engage and/or collaborate with the at least one user 122, e.g., as a paid consultant, a revenue share partner, a co-owner of created media content, pro bono, etc. via the collaboration space.

The permissions component 108 can generate and/or grant permissions to the at least one user 122 (e.g., a second user, a third user, a fourth user, etc.) to edit and/or augment (e.g., alter and/or enhance) the uploaded media content in the collaboration space. For example, the permissions component 108 can facilitate rights management (e.g., access rights) for the uploaded media content in the collaboration space. As such, the permissions component 108 can generate and/or maintain read/write permissions for the uploaded media content in the collaboration space. In one example, the permissions component 108 can determine whether the at least one user 122 is authorized to edit and/or augment the uploaded media content in the collaboration space. In another example, the permissions component 108 can establish and/or maintain permissions (e.g., privileges, authorizations, licenses, etc.) for the at least one user 122 to edit and/or augment the uploaded media content in the collaboration space.

The permissions component 108 can generate and/or grant one or more access levels associated with the uploaded media content in the collaboration space. For example, the permissions component 108 can determine types of edits and/or augmentations (e.g., types of edit functions, types of edit tasks, types of services, etc.) that can be performed by the at least one user 122. In one example, permissions for the uploaded media content can be set (e.g., determined) by the user 118. In an aspect, the permissions component 108 can set different permissions for different segments of the uploaded media content. For example, a first segment of the uploaded media content can include a first set of permissions and a second segment of the uploaded media content can include a second set of permissions. Furthermore, each user (e.g., the user 118 and/or the at least one user 122) can be associated with a different set of permissions.

The permissions component 108 can execute a set of actions based on the permissions of the at least one user 122. For example, a set of actions can include, but is not limited to, restricting or partially restricting ability of the at least one user 122 to edit and/or augment the uploaded media content in the collaboration space, modifying the uploaded media content in the collaboration space based on the permissions generated and/or granted for the at least one user 122, sending one or more notifications to the at least one user 122, etc. As such, the user 118 and/or the at least one user 122 can edit and/or augment the uploaded media content as a function a set of permissions generated and/or granted by the permissions component 108. In an aspect, the permissions component 108 can allow or deny a device associated with the at least one user 122 from accessing the collaboration space.

The finalization component 110 can generate a final version (e.g., an edited and/or augmented version) of the uploaded media content based in part on modifications made by the second user and/or the first user (e.g., the at least one user 122 and/or the user 118). For example, the finalization component 110 can generate a final version of the uploaded media content based in part on the edit(s) and/or augmentation(s) to the uploaded media content in the collaboration space. As such, a plurality of users (e.g., at least one user 122 and/or user 118) can collaboratively edit and/or augment originally uploaded media content (e.g., media content generated by a user device) to generate a final version of the uploaded media content. Accordingly, improved media content can be generated. In one example, the final version of the uploaded media content can be media content developed directly for utilization over the network 120 (e.g., media content developed directly for implementation on the web). In an aspect, the final version of the media content can be stored in the content database 116. In one example, the final version of the media content can overwrite media content originally uploaded by the user 118 (e.g., an original version of the media content stored in the content database 116).

While FIG. 1 depicts separate components in system 100, it is to be appreciated that the components may be implemented in a common component. For example, the media component 104, the collaboration component 106, the permissions component 108 and/or the finalization component 110 can be included in a single component. Further, it can be appreciated that the design of system 100 can include other component selections, component placements, etc., to facilitate collaboration for generating media content.

Figure 2:
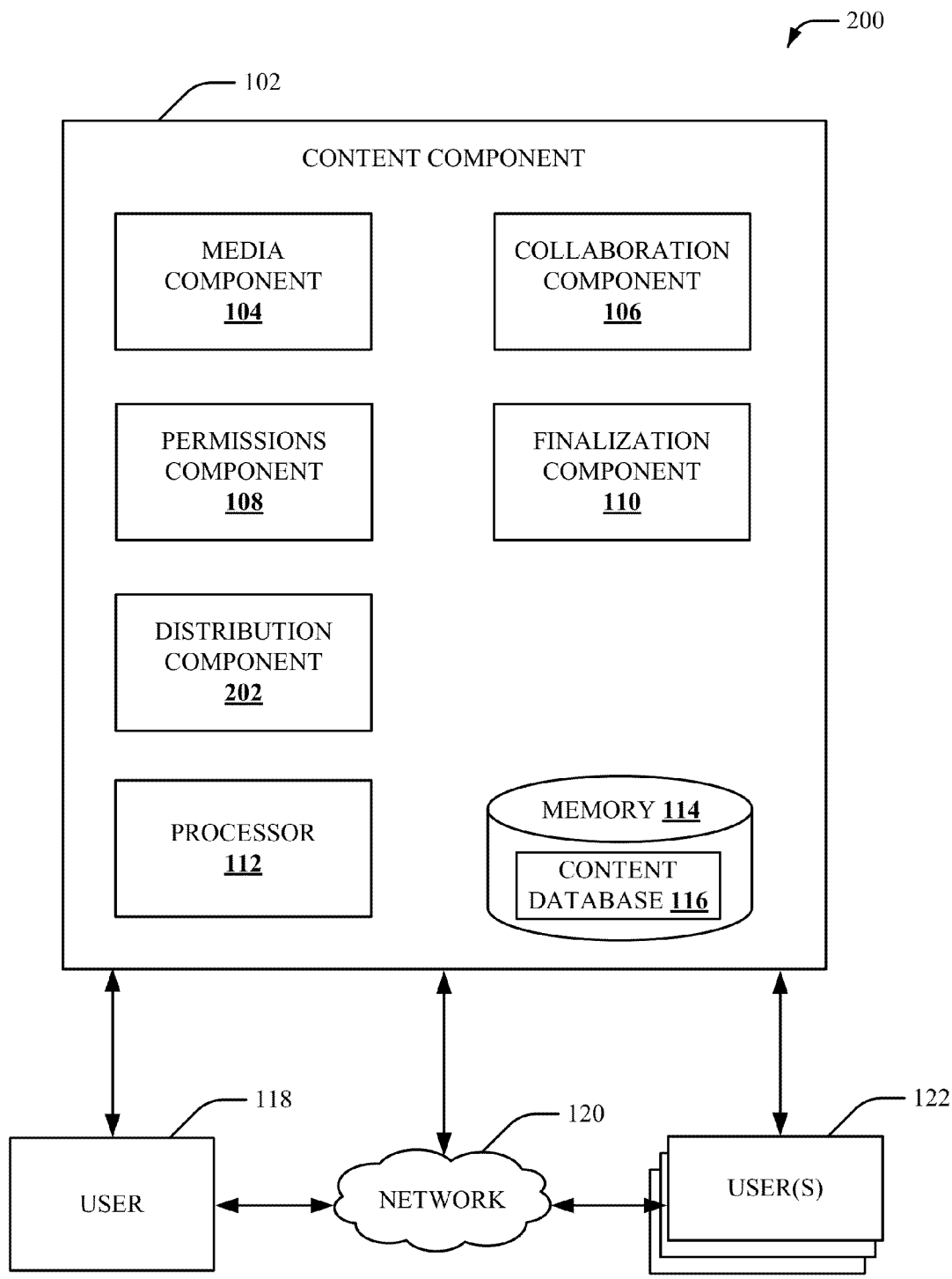
FIG. 2 illustrates a high-level block diagram of an example system to facilitate collaboration for distributing media content, in accordance with various aspects and implementations described herein.

FIG. 2 illustrates a non-limiting implementation of a system 200 in accordance with various aspects and implementations of this disclosure. The system 200 includes content component 102. The content component 102 can include the media component 104, the collaboration component 106, the permissions component 108, the finalization component 110 and/or a distribution component 202.

The distribution component 202 can distribute a partially edited version of the uploaded media content or the final version of the uploaded media content. For example, the permissions component 108 can establish and/or maintain permissions (e.g., privileges, authorizations, licenses, etc.) for the at least one user 122 to distribute and/or share a partially edited version of the uploaded media content or the final version of the uploaded media content. In an aspect, the user 118 can engage and/or collaborate with the at least one user 122, e.g., as a paid consultant, a revenue share partner, a co-owner of distributed media content, pro bono, etc. to facilitate distribution of a partially edited version of the uploaded media content or the final version of the uploaded media content.

In one example, the distribution component 202 can distribute a partially edited version of the uploaded media content or the final version of the uploaded media content to at least one server specified by the at least one user 122 (e.g., a third user). For example, the distribution component 202 can allow at least one server specified by the at least one user 122 (e.g., a third user) to access and/or store a partially edited version of the uploaded media content or the final version of the uploaded media content. The at least one user 122 (e.g., the third user) can be a different user than a user (e.g., a user 118) that uploaded the media content and/or a user (e.g., at least one user 122, a second user, etc.) that edited and/or augmented the uploaded media file. As such, a partially edited version of the uploaded media content or the final version of the uploaded media content can be distributed (e.g., shared) via the network 120. In one example, a partially edited version of the uploaded media content or the final version of the uploaded media content can be embedded on a website and/or an application not associated with the content component 102. In another example, a partially edited version of the uploaded media content or the final version of the uploaded media content can be associated with a uniform resource locator (URL) link not associated with the content component 102.

In an aspect, the distribution component 202 can determine and/or provide one or more sources that include a partially edited version of the uploaded media content or the final version of the uploaded media content. For example, the distribution component 202 can determine and/or provide an internet protocol (IP) address that includes a partially edited version of the uploaded media content or the final version of the uploaded media content, information associated with a server that includes the a partially edited version of the uploaded media content or the final version of the uploaded media content, etc. In another example, the distribution component 202 can determine and/or provide an entity that includes one or more rights (e.g., access control rights, distribution rights, consumption rights, licenses, etc.) to a partially edited version of the uploaded media content or the final version of the uploaded media content. As such, the distribution component 202 can determine and/or provide a location(s) for a partially edited version of the uploaded media content or the final version of the uploaded media content.

Figure 3:
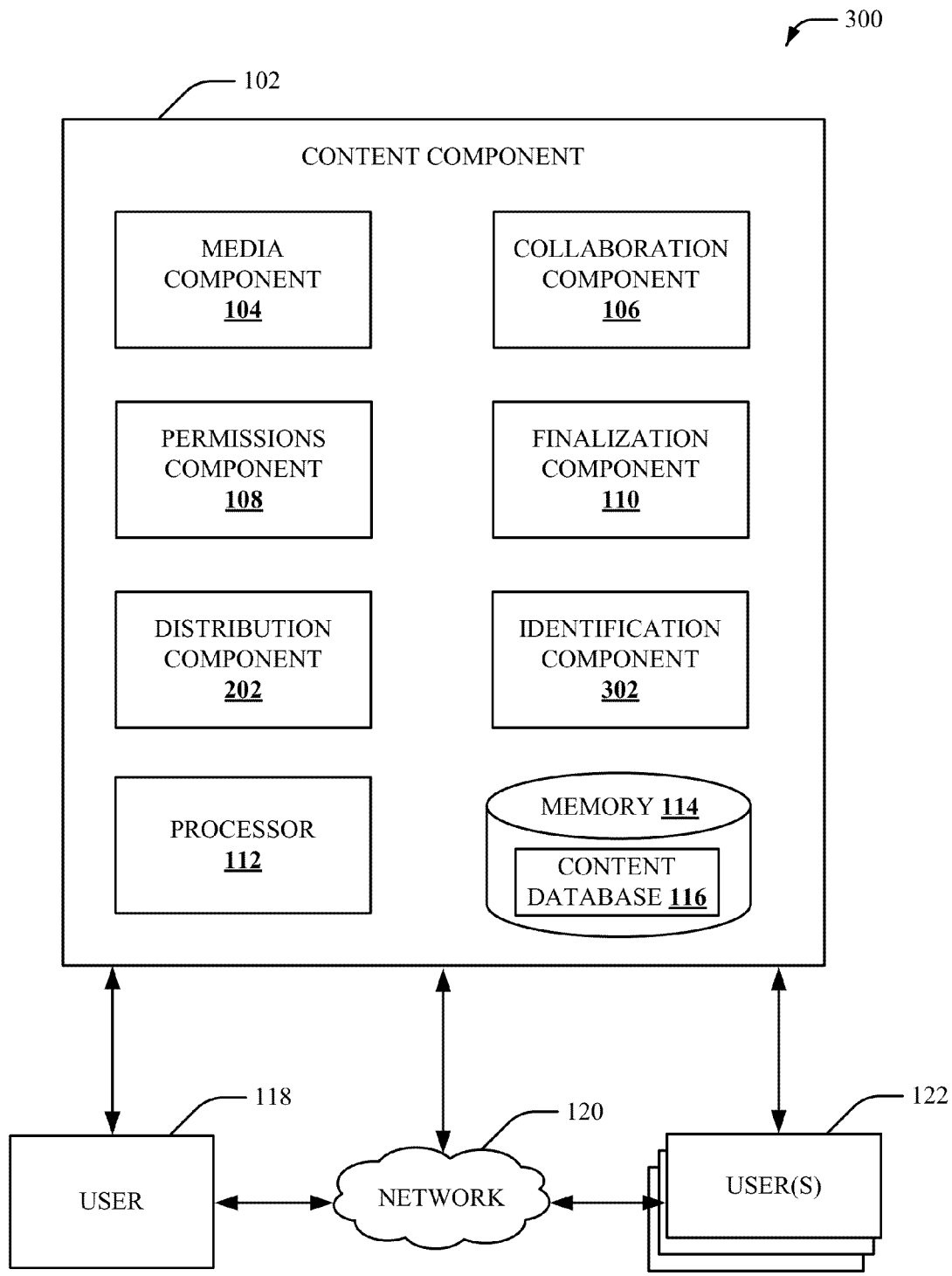
FIG. 3 illustrates a high-level block diagram of an example system to facilitate collaboration for uploading, modifying and/or sharing media content, in accordance with various aspects and implementations described herein.

FIG. 3 illustrates a non-limiting implementation of a system 300 in accordance with various aspects and implementations of this disclosure. The system 300 includes content component 102. The content component 102 can include the media component 104, the collaboration component 106, the permissions component 108, the finalization component 110, the distribution component 202 and/or an identification component 302.

The identification component 302 can identify and/or introduce the user 118 (e.g., the first user) and the at least one user 122 (e.g., the second user, the third user, etc.) in connection with collaborating to modify the uploaded media content. For example, the identification component 302 can search for particular users to collaborate with the user 118 (e.g. the user that uploaded the media content). In an aspect, the identification component 302 can identify the at least one user 122, in connection with collaborating via the online collaboration space, based on at least one editing function associated with the at least one user 122. For example, the at least one user 122 can be associated with one or more editing functions (e.g., skill sets, tasks, services, etc.) for editing and/or augmenting media content. In an aspect, the at least one user 122 (e.g., a third-party user) can be previously unknown to the user 118 (e.g., a first-party user). For example, the identification component 302 can introduce the at least one user 122 to the user 118 as a function of the at least one editing function associated with the at least one user 122. As such, the identification component 302 can facilitate dynamic collaboration for generating and/or modifying uploaded media content (e.g., the identification component 302 can facilitate dynamic collaboration for improved media content).

In an aspect, the identification component 302 can identify and/or introduce the user 118 (e.g., the first user) and the at least one user 122 (e.g., the second user, the third user, etc.) based on information associated with the uploaded media content. For example, information associated with the uploaded media content can include, but is not limited to, tag(s), metadata, subject matter identified in the uploaded media content, a budget associated with the uploaded media content, etc. As such, the identification component 302 can facilitate media content collaboration without requiring the user 118 to invite other users (e.g., the at least one user 122) to collaborate. As such, the system 300 can provide a framework to allow users that are not connected to be identified and/or collaborate together to generate improved media content.

In another aspect, the identification component 302 can identify and/or introduce the user 118 (e.g., the first user) and the at least one user 122 (e.g., the second user, the third user, etc.) based on information associated with the user 118 and/or the at least one user 122. For example, information associated with the user 118 and/or the at least one user 122 can include, but is not limited to, user reviews, user ratings, user skill sets, previous contributions to media content, fees, etc. As such, the identification component 302 can bring users with different skill sets and/or contributions together to generate improved media content. In an aspect, the identification component 302 can introduce the user 118 and the at least one user 122 (e.g., via the collaboration space, via a notification, via a message, via an email, etc.). In one example, the identification component 302 can send one or more notifications to the user 118 and/or the at least one user 122 in connection with collaborating to modify the uploaded media content. For example, the identification component 302 can send an invitation to the at least one user 122 to edit and/or share the uploaded media content (e.g., via the collaboration space, via a notification, via a message, via an email, etc.).

In an aspect, the identification component 302 can identify users that are collaborating in the collaboration space generated by the collaboration component 106. For example, the identification component 302 can generate a list of users that are contributing to edit the uploaded media content. In one example, the identification 302 can rank the list of users that are contributing to edit the uploaded media content based on, for example, percentage of contribution of a user, a monetary value associated with a user, other criterion, etc.

Figure 4:
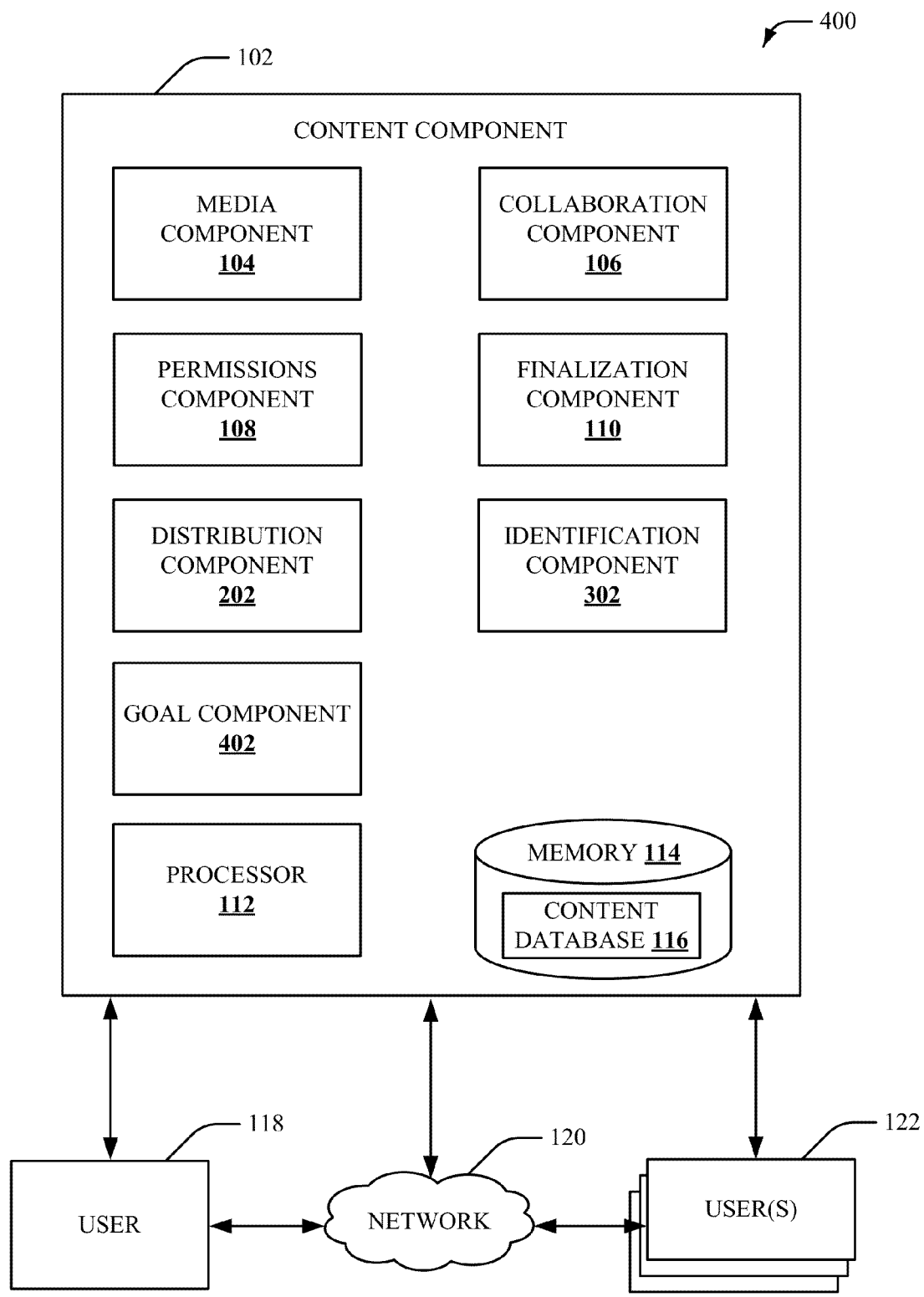
FIG. 4 illustrates a high-level block diagram of another example system to facilitate collaboration for uploading, modifying and/or sharing media content, in accordance with various aspects and implementations described herein.

FIG. 4 illustrates a non-limiting implementation of a system 400 in accordance with various aspects and implementations of this disclosure. The system 400 includes content component 102. The content component 102 can include the media component 104, the collaboration component 106, the permissions component 108, the finalization component 110, the distribution component 202, the identification component 302 and/or a goal component 402.

The goal component 402 can generate and/or publish a goal associated with the user 118 and/or the uploaded media content. For example, the user 118 can determine and/or publish a goal for the media content. Additionally, the goal component 402 can identify one or more components required to accomplish the goal. For example, the goal component 402 can determine that the uploaded media content is unprocessed media content (e.g., unedited media content, raw media content, etc.). As such, the goal component 402 can determine that the uploaded media content requires, for example, audio content, annotation, video editing, distribution, etc.

Therefore, the identification component 302 can identify at least one collaborator based on the goal generated and/or published by the goal component 402. In an aspect, the identification component 302 can identify the at least one user 122 based on the one or more components required to accomplish the goal and/or at least one editing function (e.g., skill set, task, service, etc.) associated with the at least one user 122. For example, the identification component 302 can identify and/or introduce the user 118 and the at least one user 122 as a function of the goal associated with the uploaded media content and/or the user 118 and/or at least one editing function (e.g., skill set, task, service, etc.) associated with the at least one user 122. Accordingly, the identification component 302 can identify users with particular skill sets required to accomplish the goal for the uploaded media content. As such, the goal component 402 and/or the identification component 302 can identify potential collaborators for the uploaded media content.

Figure 5:
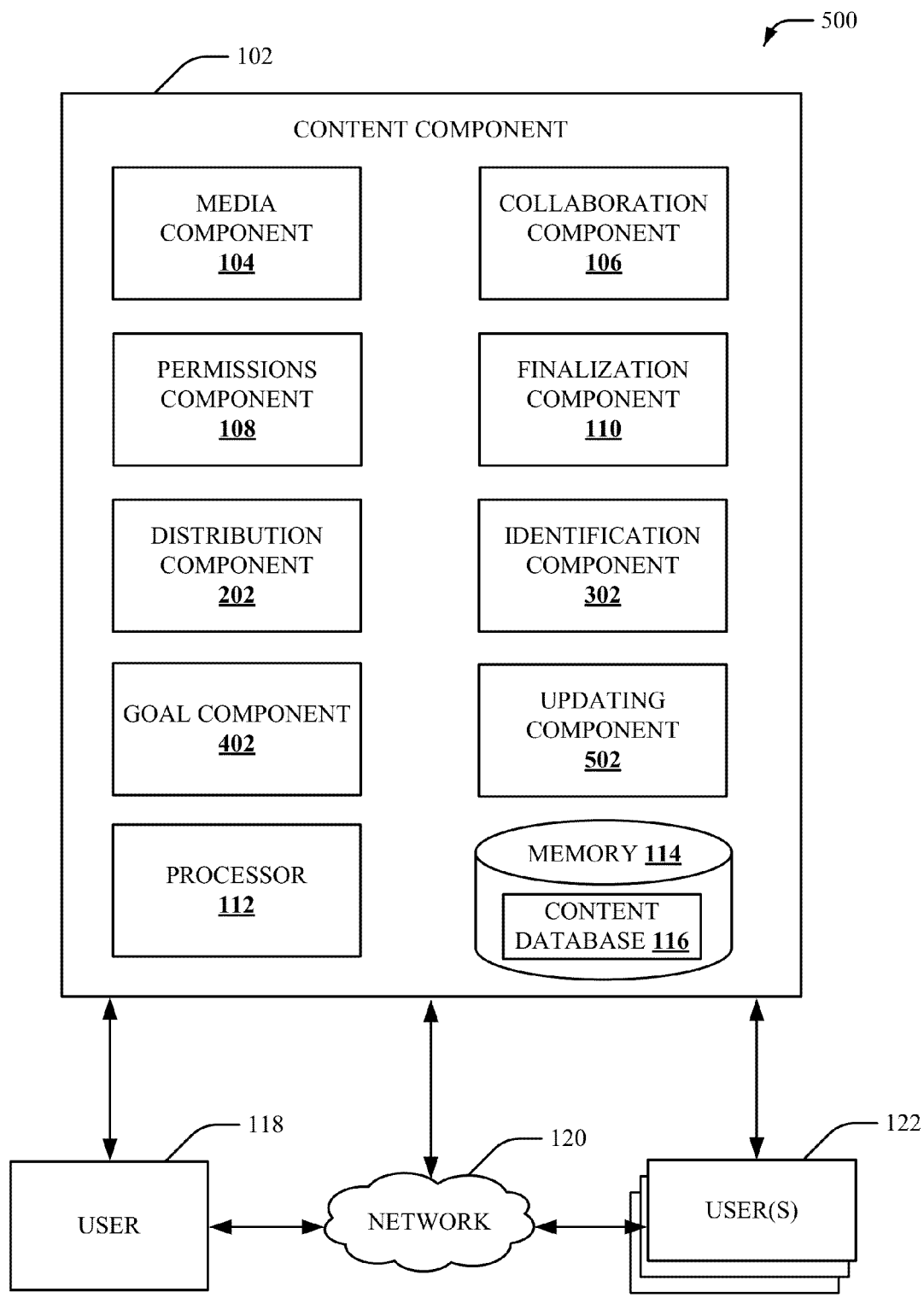
FIG. 5 illustrates a high-level block diagram of yet another example system to facilitate collaboration for uploading, modifying and/or sharing media content, in accordance with various aspects and implementations described herein.

FIG. 5 illustrates a non-limiting implementation of a system 500 in accordance with various aspects and implementations of this disclosure. The system 500 includes content component 102. The content component 102 can include the media component 104, the collaboration component 106, the permissions component 108, the finalization component 110, the distribution component 202, the identification component 302, the goal component 402 and/or an updating component 502.

The updating component 502 can allocate a budget and/or a contract for the uploaded media content. In one example, the updating component 502 can allocate a budget and/or a contract to edit, augment, enhance and/or distribute the uploaded media content as a function of the goal generated by the goal component 402. In another example, the user 118 can allocate a budget and/or a contract to edit, augment, enhance and/or distribute the uploaded media content. For example, the user 118 can provide a total cost requirement for editing, augmenting, enhancing and/or distributing the uploaded media content. In yet another example, the updating component 502 can allocate a budget and/or a contract for the uploaded media content based on one or more weights provided by the user 118. For example, the user 118 can assign a higher budget and/or a different contract to a particular aspect for editing, augmenting, enhancing and/or distributing the uploaded media content. Additionally, the updating component 502 can publish (e.g., distribute) the budget and/or the contract associated with the user 118.

In an aspect, one or more contributors (e.g., the at least one user 122) can publish one or more bids in order to collaborate with the user 118. For example, the at least one user 122 can be determined (e.g., selected) as a function of one or more bids placed by the at least one user 122. In another aspect, the identification component 302 can identify one or more potential contributors (e.g., the at least one user 122) as a function of the budget and/or contract allocated by the updating component 502. For example, the identification component 302 can identify one or more potential contributors (e.g., the at least one user 122) that meet a monetary requirement and/or a skill set requirement set by the budget and/or contract allocated by the updating component 502. In another aspect, the user 118 can engage and/or collaborate with one or more contributors (e.g., the at least one user 122), e.g., as a paid consultant, a revenue share partner, a co-owner of created media content, pro bono, etc.

Figure 6:
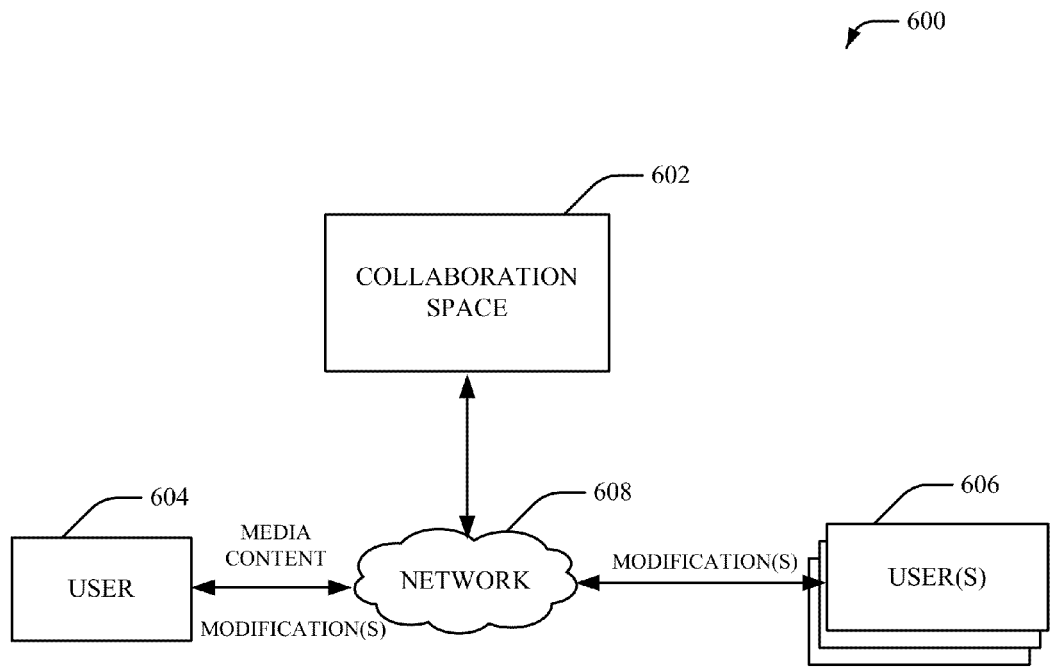
FIG. 6 illustrates example system for media content collaboration via an online collaboration space, in accordance with various aspects and implementations described herein.

Referring to FIG. 6, there is illustrated a system 600 in accordance with various aspects and implementations of this disclosure. System 600 includes a collaboration space 602, a user 604 (e.g., user 118) and at least one other user 606 (e.g., at least one user 122). The system 600 can be implemented in connection with the media component 104, the collaboration component 106, the permissions component 108, the finalization component 110, the distribution component 202, the identification component 302, the goal component 402 and/or the updating component 502. In one example, the collaboration space 602 can be implemented as an online collaboration space (e.g., via a network 608). For example, the collaboration space 602 can be implemented as a graphical user interface (GUI) accessed via a webpage and/or a network-connected application.

The user 604 can upload media content to the content component 102 (e.g., the media component 104). In response to the content component 102 (e.g., the media component 104) receiving the uploaded media content, the collaboration component 106 can generate the collaboration space 602 for the uploaded media content. For example, the collaboration space 602 can be an internet collaboration space (e.g., a cloud-based collaboration space, a web-service collaboration space, etc.). The collaboration space 602 can include functionality to modify and/or distribute the uploaded media content as a function of the user 604 and/or the at least one user 606 (e.g., the collaboration space can include a collaborative, real-time video editor). As such the collaboration space 602 can facilitate real-time editing and/or distribution of media content via the network 608.

The uploaded media content can be edited and/or augmented by the user 604 and/or the at least one other user 606 via the collaboration space 602. For example, the collaboration space 602 can receive one or more modifications from the user 604 and/or one or more modifications from the at least one other user 606. As such, the collaboration space 602 can facilitate collaborative generation of an improved version of the uploaded media content. Furthermore, the at least one user 606 can be introduced to the user 604 (e.g., via the identification component 302), as more fully disclosed herein. In an aspect, the user 604 can engage and/or collaborate with the at least one user 606, e.g., as a paid consultant, a revenue share partner, a co-owner of created media content, pro bono, etc. via the collaboration space 602. As such, the system 600 can provide a framework to allow previously unknown users and/or users with different skill sets to be introduced and/or collaborate to develop improved media content via the collaboration space 602.

Figure 7:
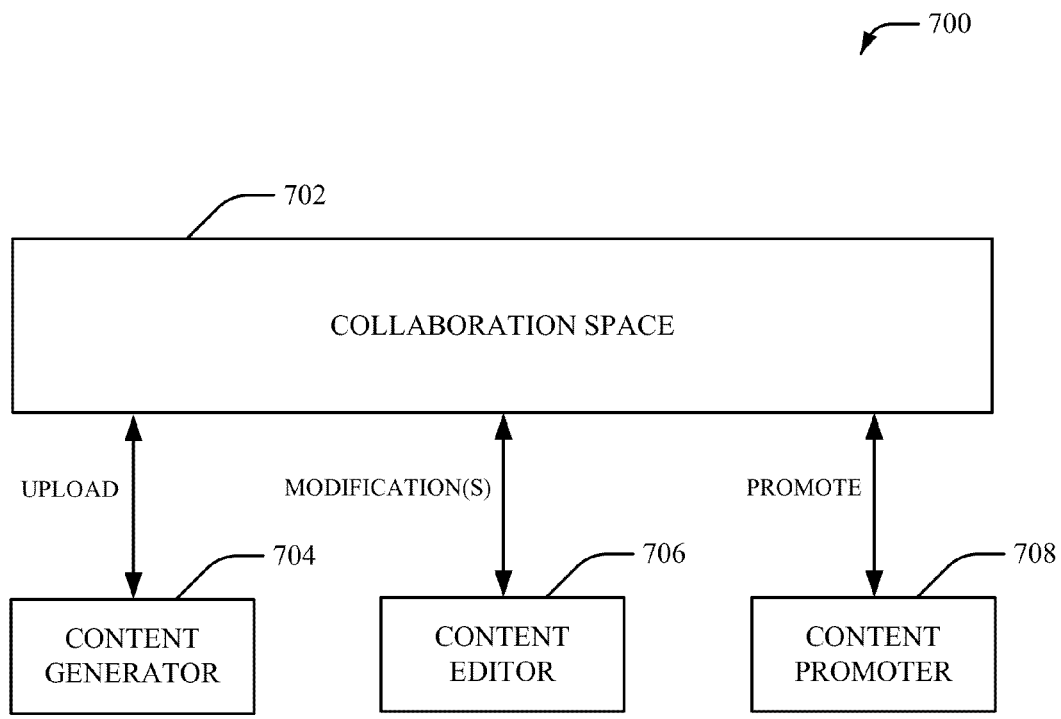
FIG. 7 illustrates an example system for media content collaboration among a plurality of users, in accordance with various aspects and implementations described herein.

Referring to FIG. 7, there is illustrated a system 700 in accordance with various aspects and implementations of this disclosure. System 700 includes a collaboration space 702 (e.g., collaboration space 602), at least one content generator 704 (e.g., user 118), at least one content editor 706 (e.g., at least one user 122) and at least one content promoter 708 (e.g., at least one user 122). The system 700 can be implemented in connection with the media component 104, the collaboration component 106, the permissions component 108, the finalization component 110, the distribution component 202, the identification component 302, the goal component 402 and/or the updating component 502.

The system 700 can facilitate collaborative, real-time media content editing (e.g., collaborative, real-time video editing). Furthermore, the system 700 can bring a plurality of media content contributors together to collaborate via the collaboration space 702. The at least one content generator 704, the at least one content editor 706 and the at least one content promoter 708 can be content contributors that can collaborate together to produce, record, edit, enhance, engage and/or promote media content. The at least one content generator 704, the at least one content editor 706 and the at least one content promoter 708 can each be individual contributors for the media content. Furthermore, the at least one content generator 704, the at least one content editor 706 and the at least one content promoter 708 can each contribute unique roles (e.g., unique roles) for media content collaboration. However, it is to be appreciated that a content contributor can be associated with more than one contribution role (e.g., an individual contributor can be a content generator 704, a content editor 706 and/or a content promoter 708).

The at least one generator 704, the at least one content editor 706 and/or the at least one content promoter 708 can be located in different locations (e.g., geographic locations). For example, the at least one content generator can be located in a first location (e.g., a first geographic location), the at least one content editor 706 can be located in a second location (e.g., a second geographic location), and the at least one content promoter 708 can be located in a third location (e.g., a third geographic location). Furthermore, at least one generator 704, the at least one content editor 706 and/or the at least one content promoter 708 can utilize different types of devices. For example, the at least one generator 704 can utilize a first device (e.g., a smartphone), the at least one content editor 706 can utilize a second device (e.g., a laptop) and the at least one content promoter 708 can utilize a third device (e.g., a tablet). The first device (e.g., smartphone) of the at least one generator 704, the second device (e.g., laptop) of the at least one content editor 706 and the third device (e.g., tablet) of the at least one content promoter 708 can each access and/or utilize the collaboration space 702 (e.g., a user interface associated with the collaboration space 702) via a webpage and/or a network-connected application.

In one example, the at least one content generator 704 can record a media file (e.g., a video file and/or an audio file). For example, the media file can be an unprocessed media file (e.g., an unedited media file, a raw media file, etc.) recorded by a non-professional videographer (e.g., a video blogger, a user of a media-sharing service, etc.). Additionally, the at least one content generator 704 can upload the media file to the collaborative space 702 (e.g., present the media file via the collaboration space 702). In an aspect, the at least one content generator 704 can engage the at least one content editor 706 and/or the at least one content promoter 708, e.g., as a paid consultant, a revenue share partner, a co-owner of created media content, pro bono, etc.

The collaboration space 702 can include a media editor (e.g., a real-time video editor). As such, the at least one content editor 706 can edit and/or augment the media file. For example, a professional videographer can manipulate the media file to generate improved media content (e.g., high end media content). In one example, the at least one content editor 706 can be previously unknown to the at least one content generator 704. For example, the at least one content editor 706 can be introduced to the at least one content generator 704 (e.g., via the identification component 302) based on an editing function (e.g., a skill set and/or service) associated with the at least one content editor 706. Therefore, the at least one content generator 704 can edit and/or augment the media file as a function of the editing function associated with the at least one content editor 706. As such, a final version of the media file can be generated.

Furthermore, the collaboration space 702 can facilitate distribution of media content (e.g., the media file). As such, the at least one content promoter 708 can promote the media file. For example, the content promoter 708 can distribute and/or promote the media file across one or more channels (e.g., media channels, network channels, websites, servers, etc.). In one example, the at least one content promoter 708 can be previously unknown to the at least one content generator 704 and/or the at least one content editor 706. For example, the at least one content promoter 708 can be introduced to the at least one content generator 704 and/or the at least one content editor 706 (e.g., via the identification component 302) based on a distribution function (e.g., a skill set and/or service) associated with the at least one content promoter 708. Therefore, the at least one content promoter 708 can promote the media file as a function of the distribution function associated with the at least one content promoter 708. As such, the collaboration space 702 (e.g., the online collaboration space) can allow a plurality of media content contributors (e.g., the at least one content generator 704, the at least one content editor 706 and the at least one content promoter 708) with different roles and/or skill sets to collaborate to generate improved media content.

Figure 8:
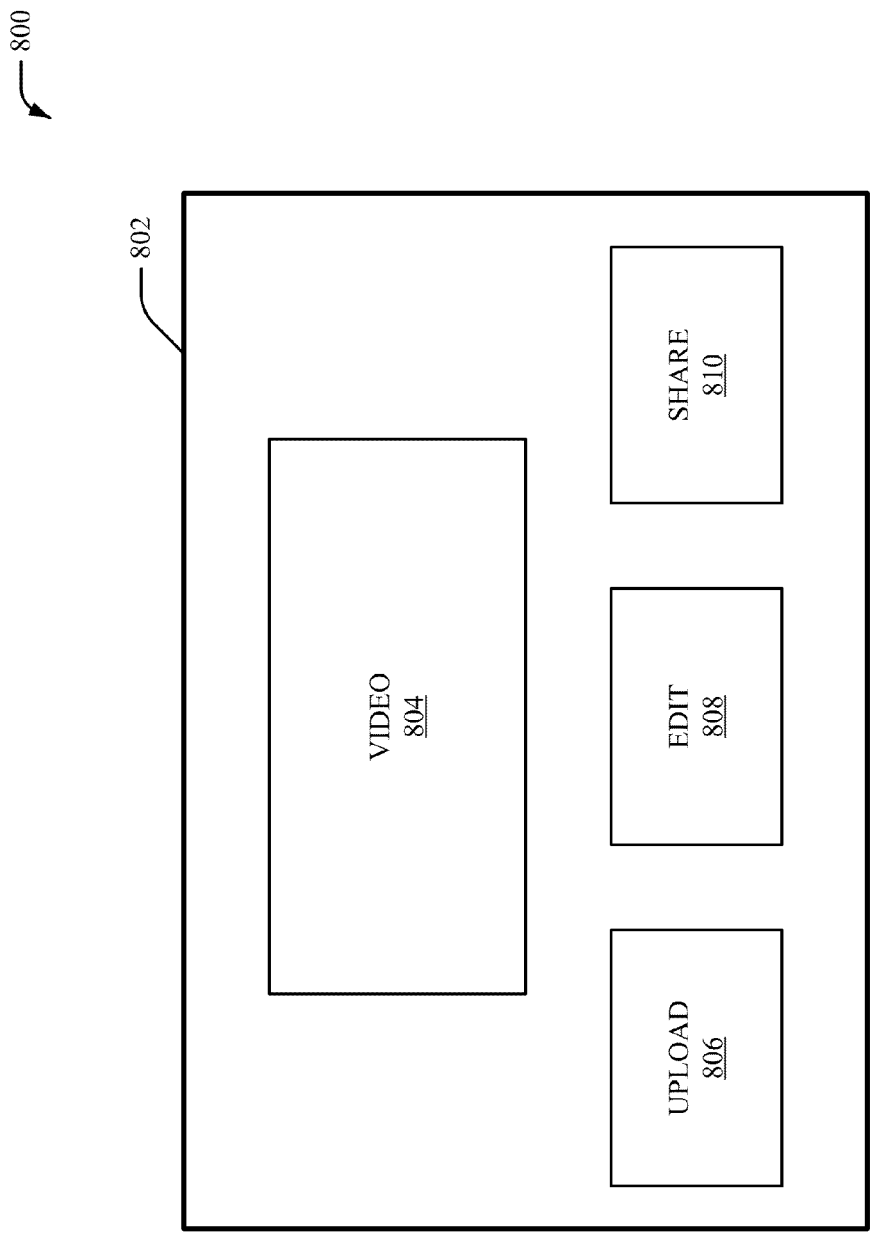
FIG. 8 illustrates an example user interface to facilitate media content collaboration, in accordance with various aspects and implementations described herein.

Referring to FIG. 8, there is illustrated a non-limiting implementation of a system 800, in accordance with various aspects and implementations of this disclosure. The system 800 can be implemented in connection with the media component 104, the collaboration component 106, the permissions component 108, the finalization component 110, the distribution component 202, the identification component 302, the goal component 402 and/or the updating component 502. The system 800 illustrates an example user interface (e.g., a graphical user interface) 802. For example, the user interface 802 can be implemented in association with a webpage and/or an application. The user interface 802 can facilitate presenting, editing and/or distributing media content. For example, the user interface 802 can implement a collaboration space (e.g., collaboration space 602 or collaboration space 702).

The user interface 802 can be implemented on and/or access via a user device. For example, user interface 802 can be implemented on and/or accessed via a cellular phone (e.g., a smartphone), a tablet, a personal computer (PC), a desktop computer, a laptop computer, a personal digital assistant (PDA), an electronic reader (e-reader), a camera, a media capable device, a portable computing device, an interactive television, an internet-connected television, a set-top box, a streaming media device, a gaming device, etc. In an aspect, the user interface 802 can be accessed and/or implemented via a web service (e.g., a cloud-based service). In an aspect, the user interface 802 can include an online video editor associated with a video hosting website. Furthermore, the user interface 802 can facilitate distribution of media content.

The user interface 802 can include an upload option 806, an edit option 808 and a share option 810. For example, a first user can upload a video 804 via the upload option 806. Additionally, the edit option 808 can include video editing functionality to edit and/or augment the video 804. As such, a second user can edit the video 804 via the edit option 808. However, it is to be appreciated that other users (e.g., the first user, a third user, etc.) can also edit the video 804 via the edit option 808. As such, the video 804 can be modified and/or distributed via the user interface 802. Furthermore, the share option 810 can facilitate distribution of the video 804 through one or more channels (e.g., media channels, network channels, servers, devices, etc.). For example, a third user can distribute the video 804 via the share option 810. However, it is to be appreciated that other users (e.g., the first user, the second user, a fourth user, etc.) can distribute the video 804 via the share option 810. As such, the video 804 can be accessed and/or stored via a plurality of locations (e.g., network locations, devices, etc.). In an aspect, the video 804 can be shared at the same time or substantially same time such that each of the respective users are consuming, editing and/or distributing the video 804 in real-time. It is to be appreciated that the user interface 802 is merely an example. As such, the user interface 802 can include other features, content and/or functionalities not shown in FIG. 8.

In an aspect, the edit option 808 can further include one or more bids associated with editing the media content (e.g., one or more bids generated and/or maintained by the updating component 502). Additionally or alternatively, the share option 810 can further include one or more bids associated with distributing the media content (e.g., one or more bids generated and/or maintained by the updating component 502). In another aspect, the edit option 808 can further include a list of collaborators that have edited and/or augmented the video 804. Additionally or alternatively, the share option 810 can further include a list of collaborators that have distributed and/or shared the video 804.

The aforementioned systems and/or devices have been described with respect to interaction between several components. It should be appreciated that such systems and/or components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

FIGS. 9-12 illustrate methodologies and/or flow diagrams in accordance with the disclosed subject matter. For simplicity of explanation, the methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device or storage media.

Figure 9:
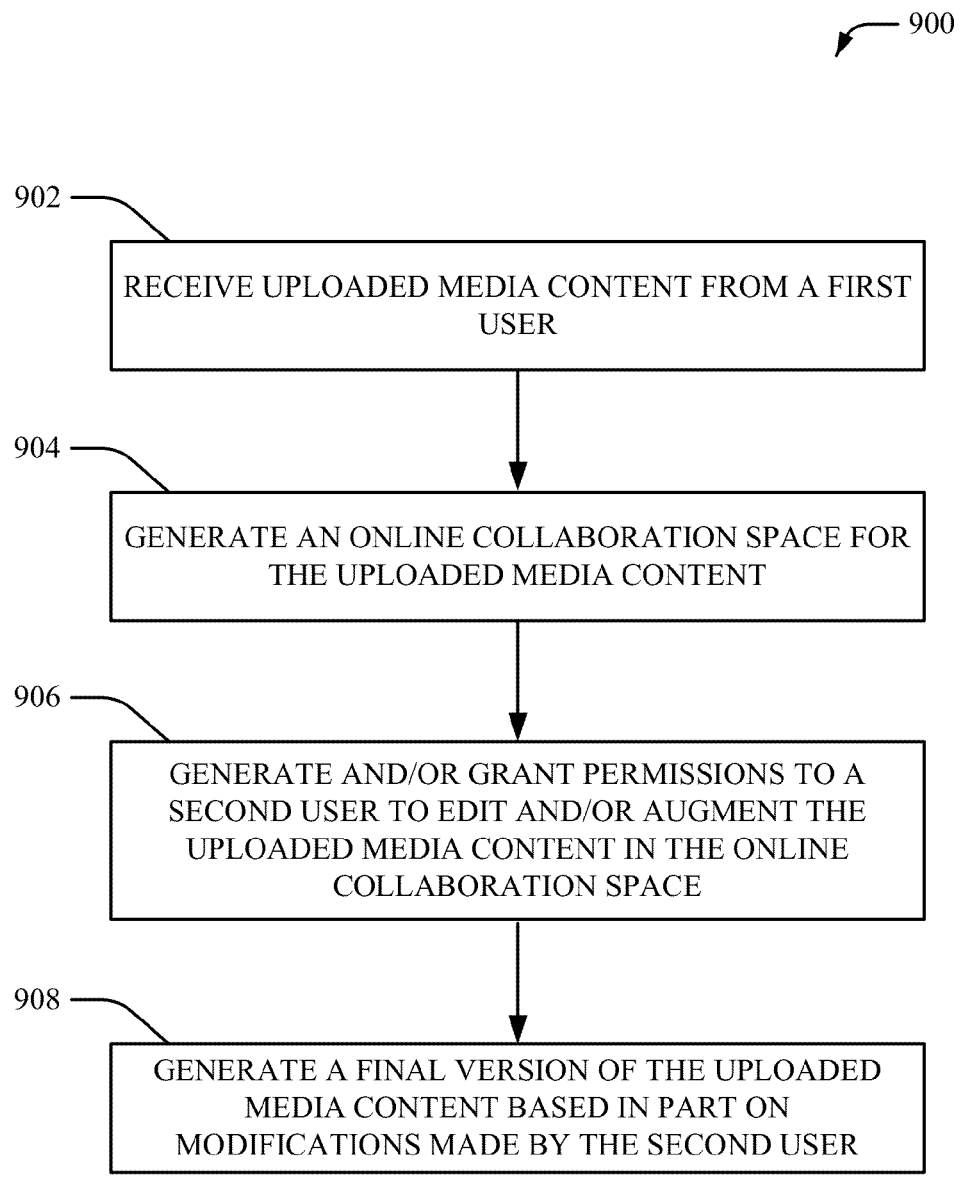
FIG. 9 depicts a flow diagram of an example method for facilitating media content collaboration, in accordance with various aspects and implementations described herein.

Referring to FIG. 9, there illustrated is a methodology 900 for facilitating media content collaboration, according to an aspect of the subject innovation. As an example, methodology 900 can be utilized in various applications, such as, but not limited to, media content systems, media server systems, cloud-based systems, content management systems, network systems, computer network systems, communication systems, router systems, server systems, high availability server systems (e.g., Telecom server systems), Web server systems, file server systems, disk array systems, powered insertion board systems, etc.

At 902, uploaded media content is received (e.g., by a media component 104) from a first user. For example, a first user (e.g., user 118) can capture (e.g., record) media content (e.g., a video) using a device. Furthermore, the first user can upload the media content (e.g., unedited media, unprocessed media, raw media, etc.) using the device or another device. The device or the other device can include, but is not limited to, a cellular phone (e.g., a smartphone), a tablet, a personal computer (PC), a desktop computer, a laptop computer, a camera, a media capable device, a portable computing device, an interactive television, an internet-connected television, a streaming media device, a gaming device, etc.

At 904, an online collaboration space is generated (e.g., using a collaboration component 106) for the uploaded media content. For example, an environment to facilitate consumption (e.g., viewing), editing and/or distribution of the uploaded media content can be generated. The online collaboration space can be accessed by the user and/or a plurality of other users. In an aspect, the online collaboration space can be presented on a graphical user interface (GUI).

At 906, permissions are generated and/or granted (e.g., by a permissions component 108) to a second user to edit and/or augment the uploaded media content in the online collaboration space. For example, access rights (read/write privileges, authorizations, licenses, etc.) can be generated and/or granted to at least one other user (e.g., at least one user 122) to edit and/or augment the uploaded media content in the online collaboration space. As such, the first user and/or at least one other user can collaboratively edit and/or augment the uploaded media content in the online collaboration space. In an aspect, the second user can be identified, in connection with collaborating via the online collaboration space, based on an editing function (e.g., a skill set, a service, etc.) associated with the second user.

At 908, a final version of the uploaded media content is generated (e.g., by a finalization component 110) based in part on modifications made by the second user. For example, an edited version of the uploaded media content can be generated by one or more users. In one example, the final version of the uploaded media content can be media content developed directly for utilization over a network (e.g., media content developed directly for implementation on the web).

Figure 10:
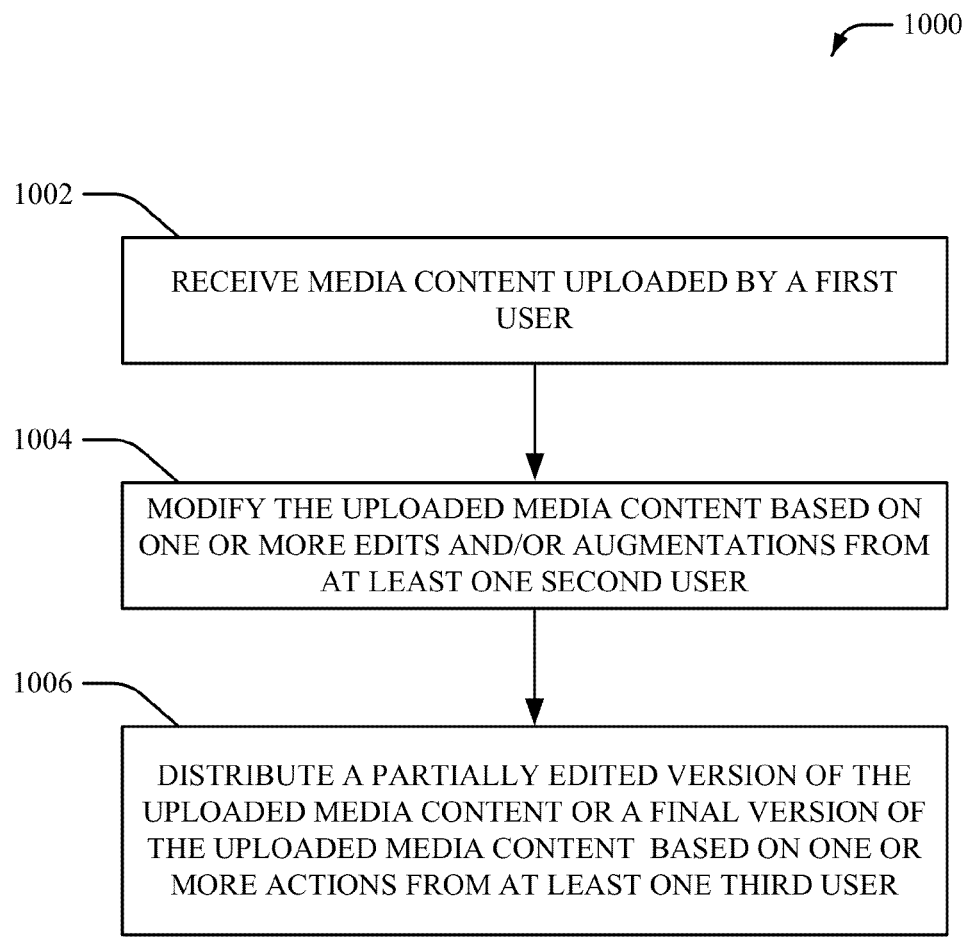
FIG. 10 depicts a flow diagram of another example method for facilitating media content collaboration, in accordance with various aspects and implementations described herein.

Referring to FIG. 10, there illustrated is an example methodology 1000 for collaboratively generating, editing and/or sharing media content. At 1002, media content uploaded by a first user is received (e.g., by a media component 104). For example, a first user (e.g., content generator 704) of a media sharing service can upload media content (e.g., a video). The first user can be located in a first location (e.g., a first geographic location). Furthermore, the first user can utilize a first user device.

At 1004, the uploaded media content is modified (e.g., using a collaboration component 106, a permissions component 108 and/or a finalization component 110) based on one or more edits and/or augmentations from at least one second user. For example, at least one second user (e.g., content editor 706) can be given permission to edit and/or augment the uploaded media content via a collaboration space (e.g., collaboration space 702). The collaboration space can facilitate the edits and/or augmentations to the uploaded media content by providing media content editing (e.g., an online video editor). The at least one second user can be located in a second location (e.g., a second geographic location). Furthermore, the at least one second user can utilize a second user device.

At 1006, a partially edited version of the uploaded media content or a final version of the uploaded media content is distributed (e.g., by a distribution component 202) based on one or more actions from at least one third user. For example, at least one third user (e.g., content promoter 708) can be given permission to distribute and/or share the uploaded media content via one or more channels (e.g., media channels, network channels, servers, devices, etc.). The at least one third user can be located in a third location (e.g., a third geographic location). Furthermore, the at least one third user can utilize a third user device.

Figure 11:
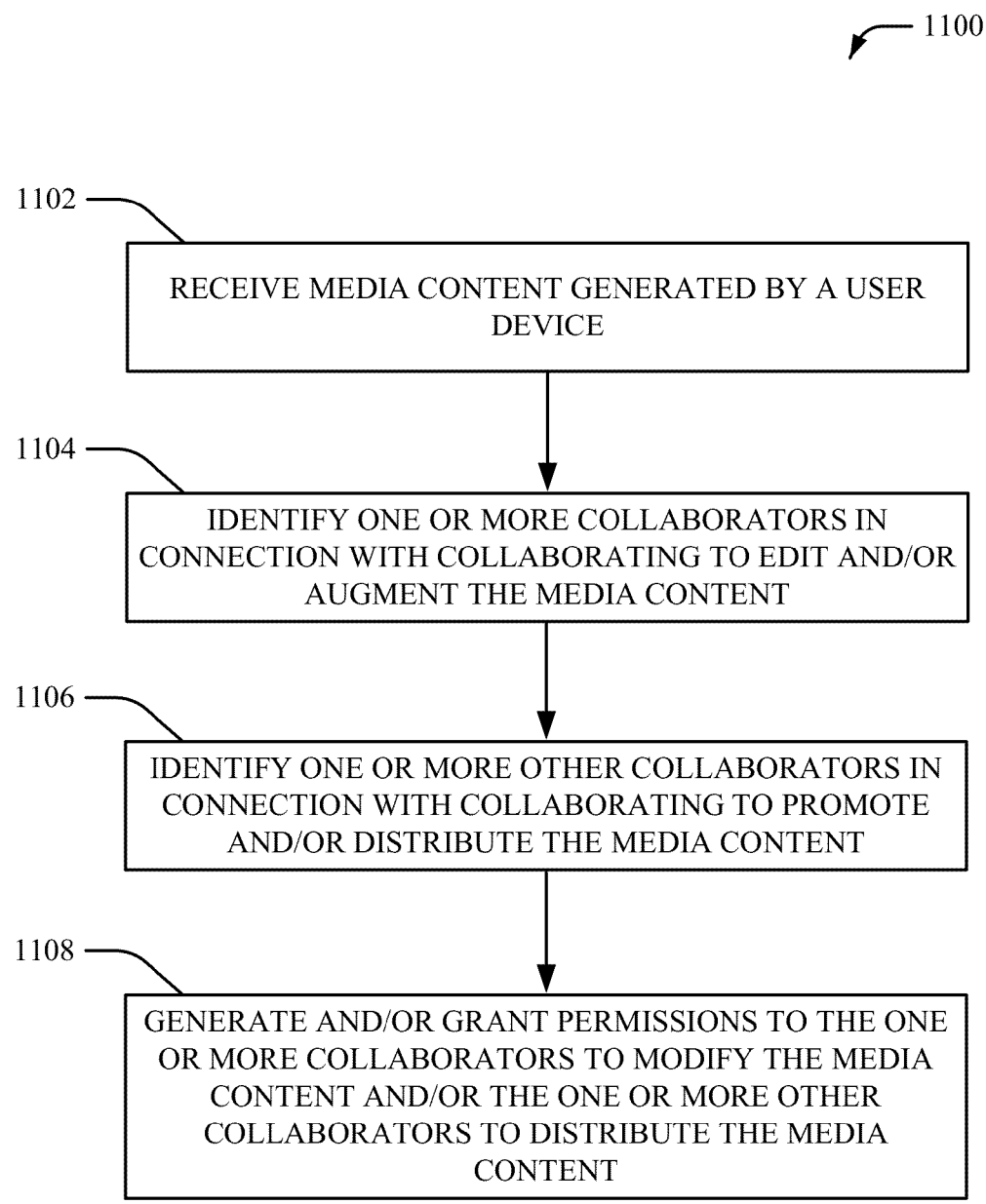
FIG. 11 depicts a flow diagram of an example method for facilitating collaborative generation, editing and/or sharing of media content, in accordance with various aspects and implementations described herein.

Referring to FIG. 11, there illustrated is an example methodology 1100 for facilitating collaborative generation, editing and/or sharing of media content. At 1102, media content uploaded generated by a user device is received (e.g., by a media component 104). For example, a user (e.g., user 118) can upload media content captured (e.g., recorded) using user device (e.g., a cellular phone, a smartphone, a tablet, a personal computer (PC), a desktop computer, a laptop computer, a camera, a media capable device, a portable computing device, an interactive television, an internet-connected television, a streaming media device, a gaming device, etc.) to the media component 102. The media content generated by the user device can be unprocessed media content (e.g., unedited media content, raw media content, etc.). The media component 102 can be associated with a media sharing service (e.g., the media component 102 can be implemented on or in connection with at least one media content server).

At 1104, one or more collaborators in connection with collaborating to edit and/or augment the media content are identified (e.g., by an identification component 302). In an aspect, one or more collaborators (e.g., at least one user 122) can be identified to edit and/or augment the media content based on information associated with the media content. For example, information associated with the media content can include, but is not limited to, tag(s), metadata, subject matter identified in the media content, a budget associated with the media content, etc. In another aspect, one or more collaborators (e.g., at least one user 122) can be identified to edit and/or augment the media content based on user information associated with a user that uploaded the media content (e.g., user 118) and/or the one or more collaborators (e.g., at least one user 122). For example, user information can include, but is not limited to, user reviews, user ratings, user skill sets, previous contributions, fees, etc.

At 1106, one or more other collaborators in connection with collaborating to promote and/or distribute the media content are identified (e.g., by an identification component 302). In an aspect, one or more other collaborators can be identified to promote and/or distribute the media content based on information associated with the media content. For example, information associated with the media content can include, but is not limited to, tag(s), metadata, subject matter identified in the media content, a budget associated with the media content, etc. In another aspect, one or more collaborators (e.g., at least one user 122) can be identified to promote and/or distribute the media content based on user information associated with a user that uploaded the media content (e.g., user 118) and/or the one or more collaborators (e.g., at least one user 122). For example, user information can include, but is not limited to, user reviews, user ratings, user skill sets, previous contributions, fees, etc.

At 1108, permissions are generated and/or granted to the one or more collaborators to modify the media content and/or the one or more other collaborators to distribute the media content. For example, rights management (e.g., access rights, edit rights, distribution rights, licenses, etc.) for the content can be generated and/or granted. In an aspect, the permissions can allow or deny the one or more collaborators from modifying the media content in a collaboration space. Additionally or alternatively, the permissions can allow or deny the one or more other collaborators from distributing the media content via a collaboration space. In another aspect, the permissions can allow or deny a device associated with the one or more other collaborators and/or the one or more other collaborators from accessing the collaboration space.

Figure 12:
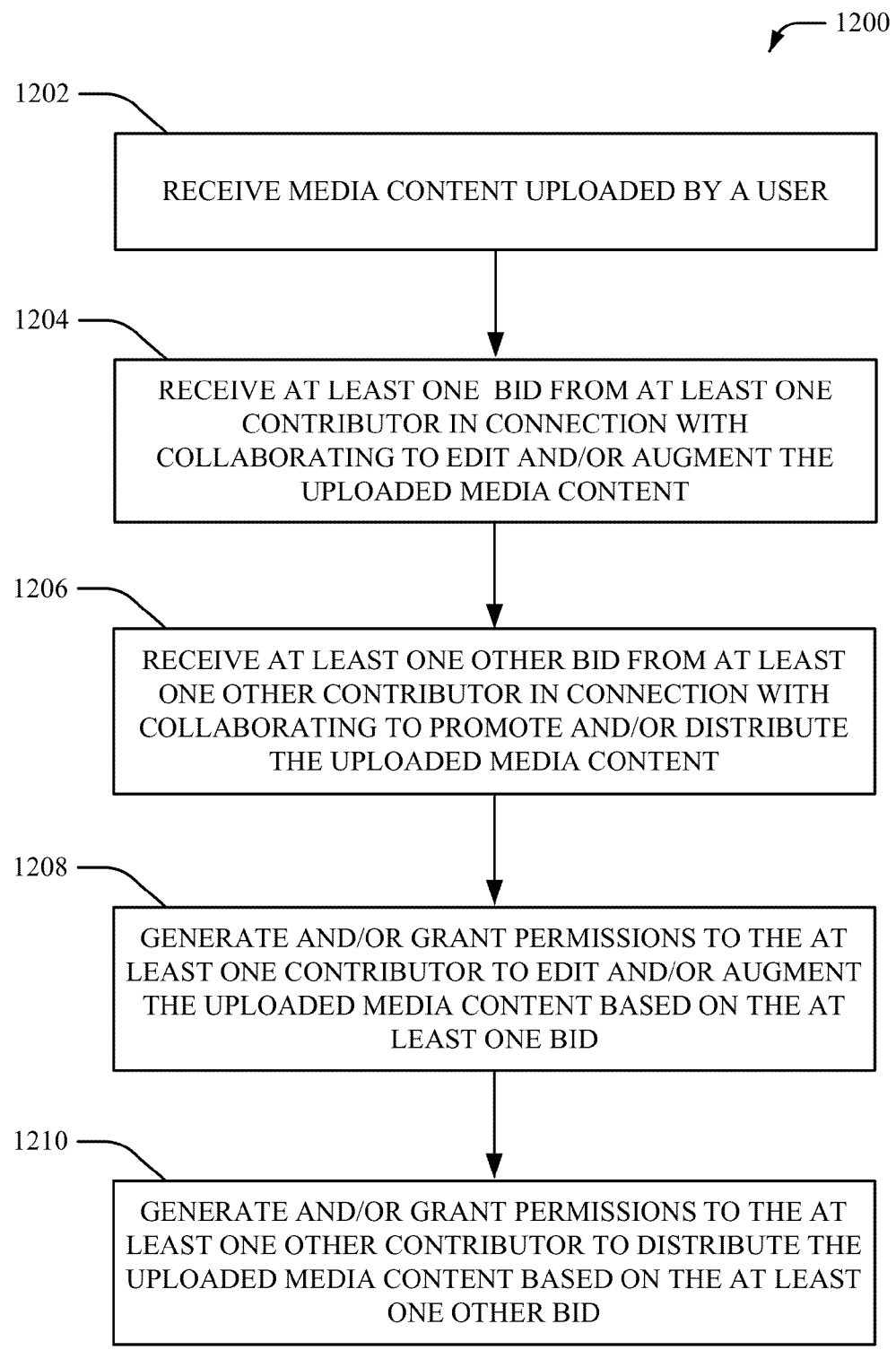
FIG. 12 depicts a flow diagram of another example method for facilitating collaborative generation, editing and/or sharing of media content, in accordance with various aspects and implementations described herein.

Referring to FIG. 12, there illustrated is an example methodology 1200 for facilitating collaborative generation, editing and/or sharing of media content. At 1202 media content uploaded by a user is received (e.g., by a media component 104). For example, a user (e.g., a user 118) can upload media content to a media component 102 associated with an online media sharing service (e.g., a media content server).

At 1204, at least one bid from at least one contributor is received (e.g., by an updating component 502) in connection with collaborating to edit and/or augment the uploaded media content. For example, at least one contributor (e.g., at least one user 122) can publish a fee in connection with collaborating for editing and/or augmenting the uploaded media content. In one example, the at least one contributor (e.g., at least one user 122) can publish a fee in connection with collaborating for editing and/or augmenting the uploaded media content based on a goal published by the user (e.g., user 118).

At 1206, at least one bid from at least one other contributor is received (e.g., by an updating component 502) in connection with collaborating to promote and/or distribute the uploaded media content. For example, at least one contributor (e.g., at least one user 122) can publish a fee in connection with collaborating for promoting and/or distributing the uploaded media content. In one example, the at least one contributor (e.g., at least one user 122) can publish a fee in connection with collaborating for promoting and/or distributing the uploaded media content based on a goal published by the user (e.g., user 118).

At 1208, permissions are generated and/or granted (e.g., by a permissions component 108) to the at least one contributor to edit and/or augment the uploaded media content based on the at least one bid. For example, in response to a determination that the at least one bid is a highest bid and/or meets a goal associated with the uploaded media content, permissions can be generated and/or granted to the at least one contributor to edit and/or augment the uploaded media content.

At 1210, permissions are generated and/or granted (e.g., by a permissions component 108) to the at least one other contributor to distribute the uploaded media content based on the at least one other bid. For example, in response to a determination that the at least one other bid is a highest bid and/or meets a goal associated with the uploaded media content, permissions can be generated and/or granted to the at least one contributor to promote and/or distribute the uploaded media content.

Figure 13:
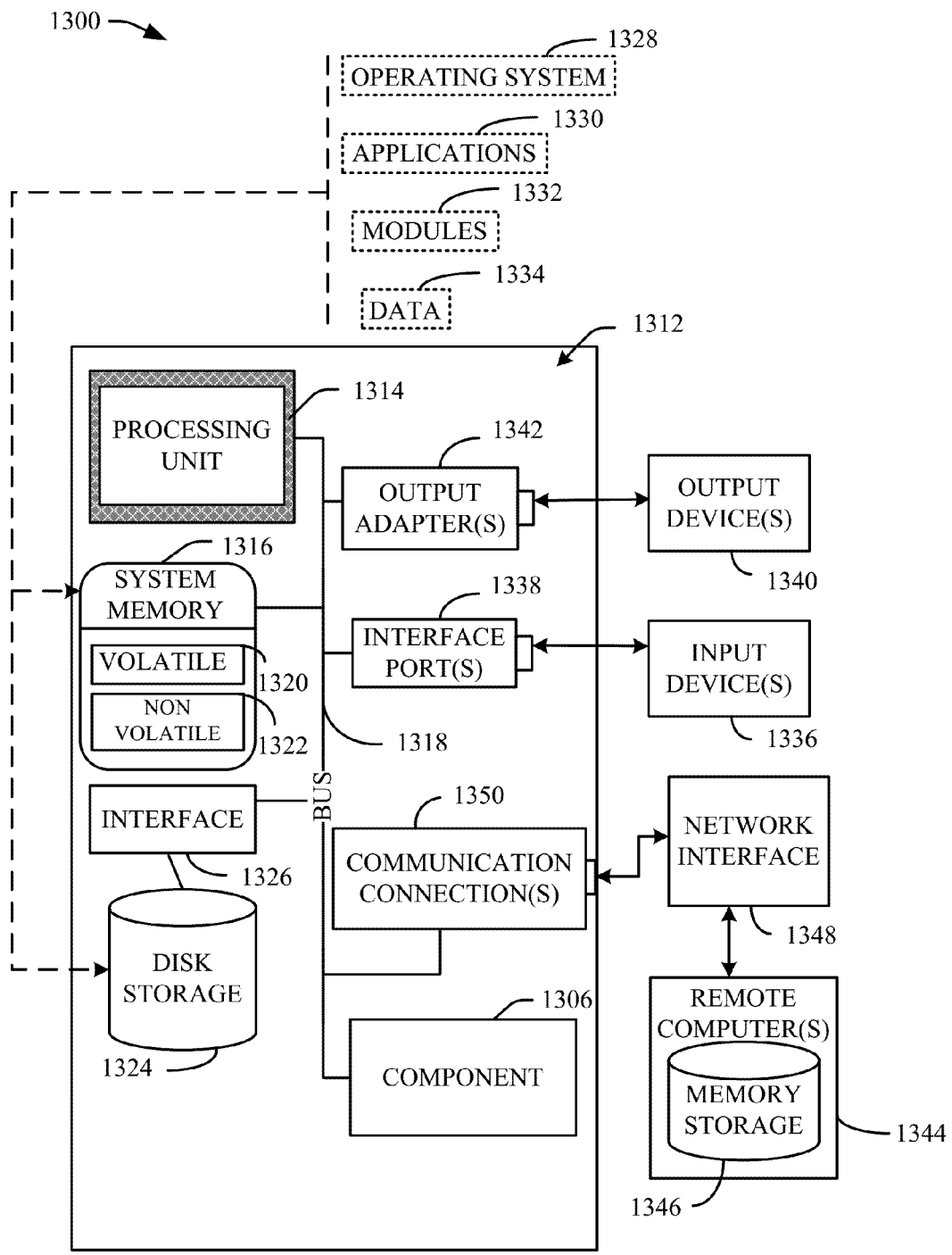
FIG. 13 is a schematic block diagram illustrating a suitable operating environment.
Figure 14:
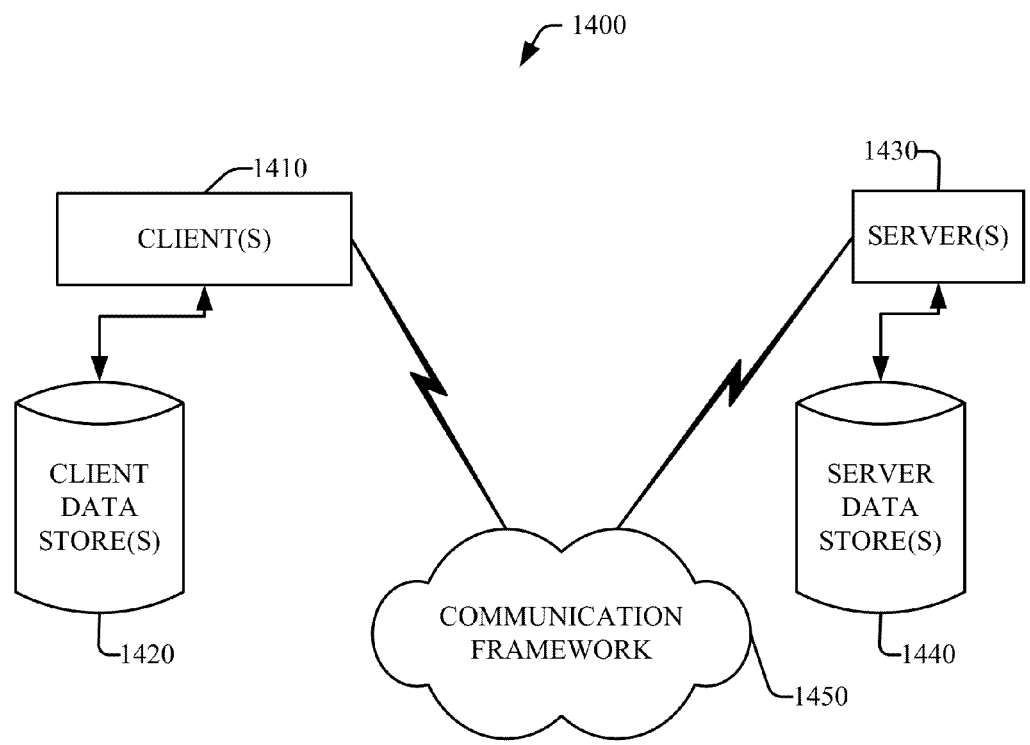
FIG. 14 is a schematic block diagram of a sample-computing environment.

In order to provide a context for the various aspects of the disclosed subject matter, FIGS. 13 and 14 as well as the following discussion are intended to provide a brief, general description of a suitable environment in which the various aspects of the disclosed subject matter may be implemented.

With reference to FIG. 13, a suitable environment 1300 for implementing various aspects of this disclosure includes a computer 1312. The computer 1312 includes a processing unit 1314, a system memory 1316, and a system bus 1318. The system bus 1318 couples system components including, but not limited to, the system memory 1316 to the processing unit 1314. The processing unit 1314 can be any of various available processors. Dual microprocessors and other multi-processor architectures also can be employed as the processing unit 1314.

The system bus 1318 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1316 includes volatile memory 1320 and nonvolatile memory 1322. The basic input/output system (BIOS), containing the basic routines to transfer information between elements within the computer 1312, such as during start-up, is stored in nonvolatile memory 1322. By way of illustration, and not limitation, nonvolatile memory 1322 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1320 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1312 also includes removable/non-removable, volatile/nonvolatile computer storage media. FIG. 13 illustrates, for example, a disk storage 1324. Disk storage 1324 includes, but is not limited to, devices like a magnetic disk drive, floppy disk drive, tape drive, Jaz drive, Zip drive, LS-100 drive, flash memory card, or memory stick. The disk storage 1324 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1324 to the system bus 1318, a removable or non-removable interface is typically used, such as interface 1326.

FIG. 13 also depicts software that acts as an intermediary between users and the basic computer resources described in the suitable operating environment 1300. Such software includes, for example, an operating system 1328. Operating system 1328, which can be stored on disk storage 1324, acts to control and allocate resources of the computer system 1312. System applications 1330 take advantage of the management of resources by operating system 1328 through program modules 1332 and program data 1334, e.g., stored either in system memory 1316 or on disk storage 1324. It is to be appreciated that this disclosure can be implemented with various operating systems or combinations of operating systems.

A user enters commands or information into the computer 1312 through input device(s) 1336. Input devices 1336 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1314 through the system bus 1318 via interface port(s) 1338. Interface port(s) 1338 include, for example, a serial port, a parallel port, a game port, and a universal serial bus (USB). Output device(s) 1340 use some of the same type of ports as input device(s) 1336. Thus, for example, a USB port may be used to provide input to computer 1312, and to output information from computer 1312 to an output device 1340. Output adapter 1342 is provided to illustrate that there are some output devices 1340 like monitors, speakers, and printers, among other output devices 1340, which require special adapters. The output adapters 1342 include, by way of illustration and not limitation, video and sound cards that provide a means of connection between the output device 1340 and the system bus 1318. It should be noted that other devices and/or systems of devices provide both input and output capabilities such as remote computer(s) 1344.

Computer 1312 can operate in a networked environment using logical connections to one or more remote computers, such as remote computer(s) 1344. The remote computer(s) 1344 can be a personal computer, a server, a router, a network PC, a workstation, a microprocessor based appliance, a peer device or other common network node and the like, and typically includes many or all of the elements described relative to computer 1312. For purposes of brevity, only a memory storage device 1346 is illustrated with remote computer(s) 1344. Remote computer(s) 1344 is logically connected to computer 1312 through a network interface 1348 and then physically connected via communication connection 1350. Network interface 1348 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1350 refers to the hardware/software employed to connect the network interface 1348 to the bus 1318. While communication connection 1350 is shown for illustrative clarity inside computer 1312, it can also be external to computer 1312. The hardware/software necessary for connection to the network interface 1348 includes, for exemplary purposes only, internal and external technologies such as, modems including regular telephone grade modems, cable modems and DSL modems, ISDN adapters, and Ethernet cards.

It is to be appreciated that the computer 1312 can be used in connection with implementing one or more of the systems or components shown and described in connection with FIGS. 1-5. In accordance with various aspects and implementations, the computer 1312 can be used to facilitate media content collaboration. In certain exemplary embodiments, the computer 1312 includes a component 1306 (e.g., content component 102) that can contain, for example, a media component, a collaboration component, a permissions component, a finalization component, a distribution component, an identification component, a goal component and/or an updating component, each of which can respectively function as more fully disclosed herein.

FIG. 14 is a schematic block diagram of a sample-computing environment 1400 with which the subject matter of this disclosure can interact. The system 1400 includes one or more client(s) 1410. The client(s) 1410 can be hardware and/or software (e.g., threads, processes, computing devices). The system 1400 also includes one or more server(s) 1430. Thus, system 1400 can correspond to a two-tier client server model or a multi-tier model (e.g., client, middle tier server, data server), amongst other models. The server(s) 1430 can also be hardware and/or software (e.g., threads, processes, computing devices). The servers 1430 can house threads to perform transformations by employing this disclosure, for example. One possible communication between a client 1410 and a server 1430 may be in the form of a data packet transmitted between two or more computer processes.

The system 1400 includes a communication framework 1450 that can be employed to facilitate communications between the client(s) 1410 and the server(s) 1430. The client(s) 1410 are operatively connected to one or more client data store(s) 1420 that can be employed to store information local to the client(s) 1410. Similarly, the server(s) 1430 are operatively connected to one or more server data store(s) 1440 that can be employed to store information local to the servers 1430.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multi-processor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," "data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components (e.g., content component, media component, collaboration component, permissions component, finalization component, distribution component, identification component, goal component, updating component, etc.), as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A system, comprising:
a memory storing computer executable components; and
a processor configured to execute the following computer executable components stored in the memory:
a media component that receives uploaded media content from a first user;
a collaboration component that generates an online collaboration space for the uploaded media content, wherein the online collaboration space is configured for collaborative real-time editing of the uploaded media content by the first user and other users;
an identification component that:
identifies a second user based on a goal of the first user with respect to editing the uploaded media content and an editing function associated with the second user with respect to the goal, and
transmits an invitation to the second user to collaboratively edit the uploaded media content with the first user in the collaboration space;
a permissions component that grants permissions to the second user to edit the uploaded media content in the online collaboration space; and
a finalization component that generates a final version of the uploaded media content based in part on at least one edit to the uploaded media content made by the second user.

2. The system of claim 1, wherein the permissions component further grants permissions to a third user to edit the uploaded media content in the online collaboration space.

3. The system of claim 1, wherein the media component receives the uploaded media content from a first mobile device associated with the first user, and the online collaboration space receives the at least one edit to the uploaded media content from a second mobile device associated with the second user.

4. The system of claim 1, comprising a distribution component that distributes a partially edited version of the uploaded media content or the final version of the uploaded media content.

5. The system of claim 4, wherein the distribution component distributes the final version of the uploaded media content to at least one server specified by a third user.

6. The system of claim 1, wherein the edit of the uploaded media content includes a video edit or an audio edit to the uploaded media content.

7. The system of claim 1, wherein the edit of the uploaded media content includes a visual enhancement to the uploaded media content.

8. The system of claim 1, wherein the edit of the uploaded media content includes reorganization of media frames of the uploaded media content.

9. The system of claim 1, wherein the identification component further introduces the first user and the second user via the online collaboration space, and wherein the second user is previously unknown to the first user.

10. The system of claim 1, wherein the identification component further identifies the second user as a function of a cost of the editing function associated with the second user.

11. A method, comprising:
receiving, by a system including a processor, uploaded media content from a first user;
generating, by the system, an online collaboration space for the uploaded media content, wherein the online collaboration space is configured for collaborative real-time editing of the uploaded media content by the first user and other users;
identifying, by the system, a second user based on a goal of the first user with respect to editing the uploaded media content and an editing function associated with the second user with respect to the goal;
transmitting, by the system, an invitation to the second user to collaboratively edit the uploaded media content with the first user in the collaboration space;
granting, by the system, permissions to the second user to edit the uploaded media content in the online collaboration space; and
generating, by the system, a final version of the uploaded media content based in part on at least one edit to the uploaded media content made by the second user.

12. The method of claim 11, further comprising:
granting permissions to a third user to edit the uploaded media content in the online collaboration space.

13. The method of claim 11, wherein the receiving further includes receiving the uploaded media content from a first device associated with the first user and receiving the at least one edit to the uploaded media content from a second device associated with the second user.

14. The method of claim 11, further comprising:
distributing a partially edited version of the uploaded media content or the final version of the uploaded media content.

15. The method of claim 14, further comprising:
distributing the partially edited version of the uploaded media content or the final version uploaded media content to at least one server specified by a third user.

16. The method of claim 11, wherein the identifying further includes identifying the second user as a function of a cost of the editing function associated with the second user.

17. A non-transitory computer-readable medium having instructions stored thereon that, in response to execution, cause a system including a processor to perform operations comprising:
receiving a video uploaded by a first user;
generating a collaboration space for the video, wherein the online collaboration space is configured for collaborative real-time editing of the video by the first user and other users;
identifying a second user based on a goal of the first user with respect to editing the uploaded media content and an editing function associated with the second user with respect to the goal;
transmitting an invitation to the second user to collaboratively edit the video with the first user in the collaboration space;
granting permissions to the second user to edit the video in the collaboration space; and
generating a final version of the video based in part on at least one edit to the uploaded media content made by the second user.

18. The system of claim 17, the operations further comprising granting permissions to a third user to edit the video in the collaboration space.

19. The system of claim 17, the operations further comprising receiving the video from a first device associated with the first user, and receiving the at least one edit to the video from a second device associated with the second user.

20. The system of claim 17, wherein the identifying further includes identifying the second user as a function of a cost of the editing function associated with the second user.

* * * * *